(12) United States Patent
Farnholtz

(10) Patent No.: US 8,172,829 B2
(45) Date of Patent: *May 8, 2012

(54) TORQUEABLE AND DEFLECTABLE MEDICAL DEVICE SHAFT

(75) Inventor: Roger Farnholtz, Fremont, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/861,269

(22) Filed: Aug. 23, 2010

(65) Prior Publication Data

US 2010/0324482 A1    Dec. 23, 2010

Related U.S. Application Data

(63) Continuation of application No. 10/804,360, filed on Mar. 19, 2004, now Pat. No. 7,780,646, which is a continuation of application No. 09/863,152, filed on May 22, 2001, now Pat. No. 6,716,207.

(51) Int. Cl.
*A61M 25/00* (2006.01)

(52) U.S. Cl. ...................................................... 604/523

(58) Field of Classification Search .................. 604/95, 604/95.01, 95.03, 95.04, 95.05, 524, 525, 604/526, 527, 528
See application file for complete search history.

(56) References Cited

U.S. PATENT DOCUMENTS

| | | |
|---|---|---|
| 4,586,923 A | 5/1986 | Gould et al. |
| 4,597,755 A | 7/1986 | Samson et al. |
| 4,664,113 A | 5/1987 | Frisbie et al. |
| 4,719,924 A | 1/1988 | Crittenden et al. |
| 4,723,936 A | 2/1988 | Buchbinder et al. |
| 4,748,969 A | 6/1988 | Wardle |
| 4,757,827 A | 7/1988 | Buchbinder et al. |
| 4,886,067 A | 12/1989 | Palermo |
| 4,898,577 A | 2/1990 | Badger et al. |
| 4,906,230 A | 3/1990 | Maloney et al. |
| 4,920,980 A | 5/1990 | Jackowski |
| 4,940,062 A | 7/1990 | Hampton et al. |
| 4,960,134 A | 10/1990 | Webster, Jr. |
| 4,998,916 A | 3/1991 | Hammerslag et al. |
| 5,057,092 A | 10/1991 | Webster, Jr. |
| 5,060,660 A | 10/1991 | Gambale et al. |
| 5,125,896 A | 6/1992 | Hojeibane |
| 5,165,421 A | 11/1992 | Fleischhacker et al. |
| 5,190,050 A | 3/1993 | Nitzsche |
| 5,195,968 A | 3/1993 | Lundquist et al. |
| 5,228,441 A | 7/1993 | Lundquist |
| 5,242,441 A | 9/1993 | Avitall |
| 5,254,088 A | 10/1993 | Lundquist et al. |
| 5,255,679 A | 10/1993 | Imran |
| 5,271,382 A | 12/1993 | Chikama |
| 5,277,199 A | 1/1994 | DuBois et al. |

(Continued)

*Primary Examiner* — Nicholas Lucchesi
*Assistant Examiner* — Aarti B Berdichevsky
(74) *Attorney, Agent, or Firm* — Seager, Tufte & Wickhem, LLC

(57) ABSTRACT

A medical device shaft for connection with a handle and for insertion within a body includes an elongated, deflectable shaft having a proximal shaft portion, an intermediate shaft portion, and a distal shaft portion. The elongated, deflectable shaft includes a transition in stiffness from the proximal shaft portion to the distal shaft portion. In a preferred implementation, the shaft includes a plurality of slits that extend perpendicular to a longitudinal axis of the shaft. Varying at least one of the number of slits, the location of slits, the frequency of slits, the orientation of the slits, the size of the slits, and the depth of the slits varies the transition of stiffness.

2 Claims, 2 Drawing Sheets

U.S. PATENT DOCUMENTS

| | | |
|---|---|---|
| 5,279,596 A | 1/1994 | Castaneda et al. |
| 5,318,525 A | 6/1994 | West et al. |
| 5,318,526 A | 6/1994 | Cohen |
| 5,318,528 A | 6/1994 | Heaven et al. |
| 5,327,905 A | 7/1994 | Avitall |
| 5,334,145 A | 8/1994 | Lundquist et al. |
| 5,334,169 A | 8/1994 | Brown et al. |
| 5,354,297 A | 10/1994 | Avitall |
| 5,368,564 A | 11/1994 | Savage |
| 5,383,852 A | 1/1995 | Stevens-Wright |
| 5,431,168 A | 7/1995 | Webster, Jr. |
| 5,437,288 A | 8/1995 | Schwartz et al. |
| 5,462,527 A | 10/1995 | Stevens-Wright et al. |
| 5,472,017 A | 12/1995 | Kovalcheck |
| 5,487,757 A | 1/1996 | Truckai et al. |
| 5,489,270 A | 2/1996 | van Erp |
| 5,514,108 A | 5/1996 | Stevens |
| 5,545,200 A | 8/1996 | West et al. |
| 5,562,619 A | 10/1996 | Mirarchi et al. |
| 5,571,085 A | 11/1996 | Accisano, III |
| 5,573,520 A | 11/1996 | Schwartz et al. |
| 5,599,319 A | 2/1997 | Stevens |
| 5,642,736 A | 7/1997 | Avitall |
| 5,656,030 A | 8/1997 | Hunjan et al. |
| 5,662,606 A | 9/1997 | Cimino et al. |
| 5,702,373 A | 12/1997 | Samson |
| 5,741,320 A | 4/1998 | Thornton et al. |
| 5,741,429 A | 4/1998 | Donadio, III et al. |
| 5,807,249 A | 9/1998 | Qin et al. |
| 5,820,592 A | 10/1998 | Hammerslag |
| 5,823,955 A | 10/1998 | Kuck et al. |
| 5,826,576 A * | 10/1998 | West ............................ 600/373 |
| 5,865,800 A | 2/1999 | Mirarchi et al. |
| 5,882,333 A | 3/1999 | Schaer et al. |
| 5,891,114 A | 4/1999 | Chien et al. |
| 5,897,529 A | 4/1999 | Ponzi |
| 5,897,537 A | 4/1999 | Berg et al. |
| 5,906,590 A | 5/1999 | Hunjan et al. |
| 5,951,539 A | 9/1999 | Nita et al. |
| 5,971,975 A | 10/1999 | Mills et al. |
| 6,013,052 A | 1/2000 | Durman et al. |
| 6,077,258 A | 6/2000 | Lange et al. |
| 6,165,152 A | 12/2000 | Becker et al. |
| 6,251,092 B1 | 6/2001 | Qin et al. |
| 6,716,207 B2 | 4/2004 | Farnholtz |
| 7,780,646 B2 * | 8/2010 | Farnholtz ...................... 604/523 |
| 2002/0082585 A1 * | 6/2002 | Carroll et al. .................. 604/528 |

* cited by examiner

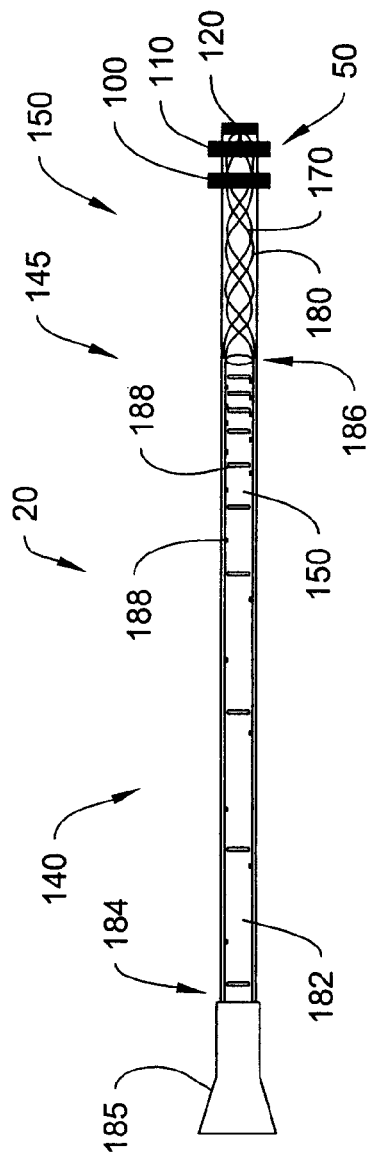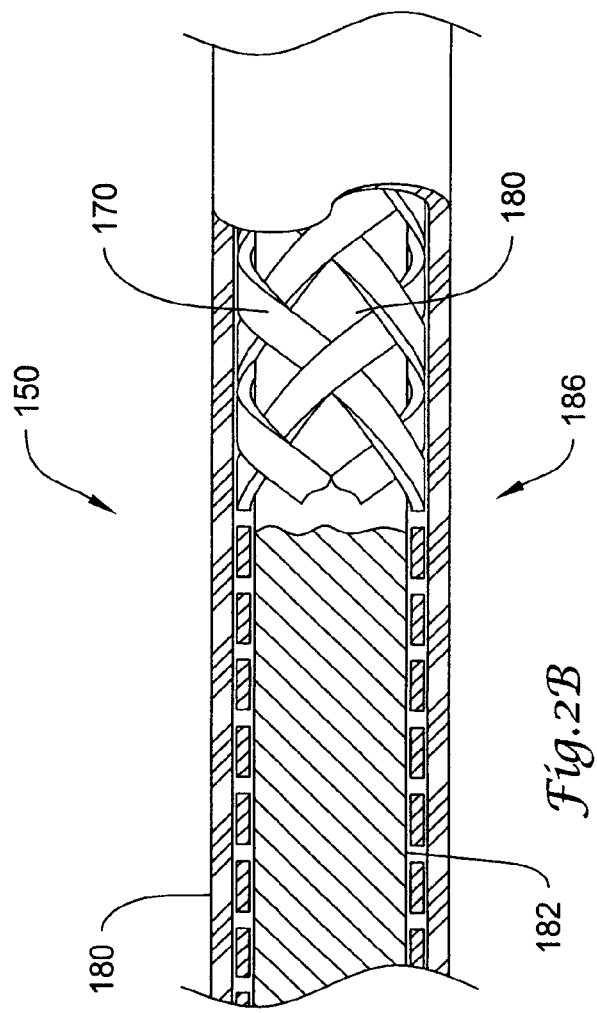

US 8,172,829 B2

TORQUEABLE AND DEFLECTABLE MEDICAL DEVICE SHAFT

CROSS REFERENCE TO RELATED APPLICATIONS

This application is a continuation of U.S. Application Ser. No. 10/804,360, filed Mar. 19, 2004, now U.S. Pat. No. 7,780,646, which is a continuation of U.S. application Ser. No. 09/863,152, filed May 22, 2001, now U.S. Pat. No. 6,716,207, the entire disclosures of which are both incorporated herein by reference.

FIELD OF THE INVENTION

The present invention relates, in general, to deflectable medical device shafts, and, in particular, to deflectable catheter shafts.

BACKGROUND OF THE INVENTION

In order to facilitate the advancement of catheters through body lumens such as an artery, deflectable catheters have been developed. The simultaneous application of torque at the proximal portion of the catheter and the ability to selectively deflect the distal tip of the catheter in a desired direction permits the physician to adjust the direction of advancement of the distal portion of the catheter, as well as to position the distal portion of the catheter during, for example, delivery of an occlusive implant.

A physician may manipulate the proximal portion of the catheter to guide the catheter through the vasculature. The deflection of the distal tip is typically provided by one or more steering wires that are attached at the distal portion of the catheter and extend to a control handle that controls the application of tension in the steering wires. In order to maneuver around turns and bends in the vasculature, the physician observes the catheter fluoroscopically, and selectively deflects the tip and rotates the proximal portion of the catheter shaft.

It is critically important to have sufficient flexibility in the distal portion of the catheter shaft so that when the catheter is advanced through a blood vessel, the catheter may follow the inherent curvature of the vessel without puncturing the vessel wall. However, it is also important to maintain stiffness in the proximal portion of the catheter shaft to allow the distal portion of the catheter to be manipulated by the physician. Therefore, there exists a need for a catheter shaft having a flexible, atraumatic distal portion while maintaining a sufficiently stiff proximal portion.

SUMMARY OF THE INVENTION

An aspect of the invention involves a medical device shaft for connection with a handle and for insertion within a body. The medical device shaft includes an elongated, deflectable shaft having a proximal shaft portion, an intermediate shaft portion, and a distal shaft portion. The elongated, deflectable shaft includes a transition in stiffness from the proximal shaft portion to the distal shaft portion. In a preferred implementation, the shaft includes a plurality of slits that extend perpendicular to a longitudinal axis of the shaft. Varying at least one of the number of slits, the location of slits, the frequency of slits, the orientation of the slits, the size of the slits, and the depth of the slits varies the transition of stiffness.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the present invention, in which similar elements are referred to by common reference numerals.

FIG. 2A is a side-elevational view of a catheter shaft constructed in accordance with an embodiment of the invention with portions of the catheter shaft cut away; and FIG. 2B is a side-elevational view of a portion of the catheter illustrated in FIG. 2A.

DETAILED DESCRIPTION OF THE PREFERRED EMBODIMENTS

Figure 1:
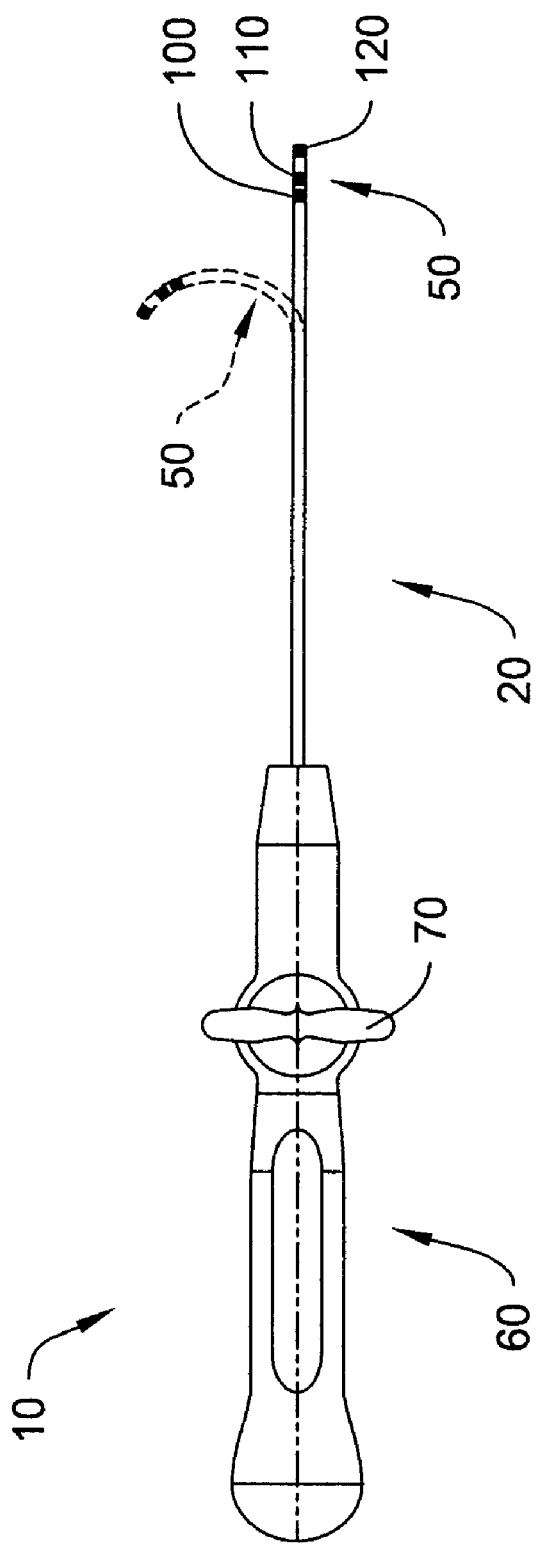
FIG. 1 is a side-elevational view of an exemplary catheter having a catheter shaft constructed in accordance with an embodiment of the invention.

With reference to FIG. 1, a catheter 10 including a torqueable and deflectable shaft or body 20 constructed in accordance with an embodiment of the present invention will now be described. The catheter 10 will first be generally described before describing the torqueable and deflectable shaft or body 20. The catheter shaft 20 will be described as being used within the vascular system of a patient; however, the catheter shaft 20 may be used within other lumens, passages, ducts, tracts, openings, etc. in the body other than blood vessels. Further, the shaft 20 may be a torqueable and deflectable shaft or body of a medical device other than a catheter.

The catheter body 20 includes an operative distal tip portion 50. The catheter 10 further includes a catheter handle 60 with a steering knob 70 to control the distal tip portion 50 of the catheter body 20 when guiding the distal tip portion 50 through the vascular system of the body. The steering knob 70 is attached to steering wires that extend through an interior lumen of the catheter body 20. The steering wires terminate and are anchored near the distal tip portion 50 so that rotation of the steering knob 70 causes deflection and bending of the shaft 20 near the distal portion 50 as shown.

The operative distal tip portion 50 may take any known construction in the art. For example, but not by way of limitation, the operative distal tip portion 50 may include an implantable and detachable occlusion device, a probe assembly, an expandable basket assembly, an expandable balloon or body, one or more electrodes for sensing, pacing, and/or ablating, one or more markers for identifying the distal tip portion, an imaging device, and any combination of the above. In the embodiment of the operative distal tip portion shown, two ring electrodes 100, 110 are disposed along the length of the distal tip portion 50 to provide radio frequency energy for ablation and/or sensing of electrical activity in body tissue. In addition, a radiopaque marker band 120 is secured to the distal tip portion 50 to facilitate visualization of the distal tip portion 50 inside the body using fluoroscopy.

FIGS. 2A and 2B relate to illustrate the body or shaft 20 of FIG. 1 in more detail. The shaft 20 includes a proximal shaft portion 140, an intermediate shaft portion 145, and a distal shaft portion 150. The shaft increases in flexibility from the proximal shaft portion 140 to the distal shaft portion 150. The distal shaft portion 150 includes the distal tip portion 50 and is comprised of a ribbon braid 170 of counter-wound double Nitinol wires embedded in a layer of hydrophobic polymer 180 to prevent the braiding 170 from being exposed. The polymer layer 180 may be covered with a hydrophilic coating.

This construction allows the distal shaft portion 150 to be flexible or bendable in a lateral direction to facilitate steering of the shaft 20, but has enough torsional strength to allow torque to be efficiently transmitted by the user from the handle to the distal shaft portion 150 without give in the shaft 150.

The ribbon braid 170 is preferably made from Nitinol in order to create a shaft that minimizes kinking, transmits a high amount of torque, and retains its shape after being bent. Importantly, a Nitinol braid 170 allows increased flexibility in the distal tip portion 50, but keeps the interior lumen from collapsing by inhibiting kinking Additionally, because Nitinol is a memory metal, a user may easily maintain the distal tip portion 50 in a desired shaped throughout a surgical procedure. In other embodiments, the braid 170 may be made of different materials such as metal alloys (e.g., stainless steel, carbon fiber).

The proximal shaft portion 140 and intermediate shaft portion 145 are preferably made of a substantially hollow Nitinol tubing 182 coated with the hydrophobic polymer layer 180. The polymer layer 180 may be covered with a hydrophilic coating. The Nitinol tubing 182 is designed to transmit torque to provide a substantially one-to-one correspondence between rotation of the proximal shaft portion 140 and distal shaft portion 150. The Nitinol tube 182 provides the shaft 150 with sufficient flexibility for advancing the shaft 150 through a tortuous lumen path and sufficient torsional strength to efficiently transmit torque from the handle 60 to the distal shaft 150. The tube 182 is also preferably made of Nitinol to minimize kinking and because Nitinol is a memory metal that retains its shape after being bent. In other embodiments, the tube 182 may be a made of a material other than Nitinol such as, but not by way of limitation, carbon fiber or a metal alloy such as stainless steel.

The shaft 20 increases in flexibility from a proximal junction 184, where the shaft 20 meets a luer attachment 185, to a distal junction 186, where the Nitinol tube 182 attaches to the Nitinol braid 170 of the distal shaft portion 150. The increase in flexibility is created by making a plurality of slits or cuts 188 along the hollow tube 182. These slits 188 extend perpendicular to a longitudinal axis of the shaft 20. An increase in flexibility in the shaft 20 from the proximal junction 184 to the distal junction 186 may be achieved by increasing the depth of the slits 188 as one progresses from the proximal junction 184 to the distal junction 186 and/or by increasing the number of slits 188 per unit length of tube 182 as one progresses from the proximal junction 184 to the distal junction 186. As best seen in FIG. 2A, the number of slits 188 per length of tube increases gradually from the proximal shaft portion 140 to the distal junction 186. Additionally, the slits 188 become increasingly deeper toward the distal junction 186. As a result, a transition in stiffness is formed, whereby the shaft 20 becomes progressively more flexible from proximal shaft portion 140 to distal shaft portion 150. The number of slits 188, location of slits 188, frequency of slits 188, orientation of the slits 188, size of the slits 188, and/or depth of the slits 188 may be varied to vary the transition of stiffness according to the desired application of the shaft 20.

While preferred embodiments and methods have been shown and described, it will be apparent to one of ordinary skill in the art that numerous alterations may be made without departing from the spirit or scope of the invention. Therefore, the invention is not limited except in accordance with the following claims.

What is claimed:

1. A medical device, comprising:
    an elongated tubular member including a proximal end and a distal end;
    a braided member attached to the distal end of the elongated tubular member and extending distally therefrom; and
    a plurality of slits defined in the tubular member and extending perpendicularly to a longitudinal axis of the tubular member; and
    a first polymer layer disposed over the elongated tubular member;
    wherein at least one of the number of slits, the location of slits, the frequency of slits, the orientation of the slits, the size of the slits and the depth of the slits are varied to vary the stiffness of the proximal and intermediate portions of the tubular member; and
    wherein at least a portion of the braided member is disposed over and contacting the first polymer layer.

2. The medical device of claim 1, further comprising a second polymer layer disposed over the tubular member and the braided member.

* * * * *